United States Patent
Yoo et al.

(10) Patent No.: US 7,648,838 B2
(45) Date of Patent: Jan. 19, 2010

(54) CELL LYSIS METHOD BY IMMOBILIZED METAL-LIGAND COMPLEX

(75) Inventors: Chang-eun Yoo, Seoul (KR); Joon-ho Kim, Gyeonggi-do (KR); Kyu-youn Hwang, Incheon-si (KR); Hun-joo Lee, Seoul (KR); Hee-kyun Lim, Gyeonggi-do (KR); Soo-min Ma, Gyeonggi-do (KR); Nam Huh, Seoul (KR); Soo-suk Lee, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 579 days.

(21) Appl. No.: 11/267,005

(22) Filed: Nov. 4, 2005

(65) Prior Publication Data
US 2006/0099711 A1     May 11, 2006

(30) Foreign Application Priority Data
Nov. 8, 2004   (KR) ............... 10-2004-0090497

(51) Int. Cl.
*G01N 33/48*   (2006.01)
*G01N 33/20*   (2006.01)
*G01N 1/00*    (2006.01)

(52) U.S. Cl. ............ 436/63; 436/73; 436/80; 436/81; 436/84; 436/174; 435/2

(58) Field of Classification Search .......... 436/63, 436/73, 80, 81, 84, 174; 435/2
See application file for complete search history.

(56) References Cited

U.S. PATENT DOCUMENTS 5,374,522 A * 12/1994 Murphy et al. ............ 435/6
5,632,904 A *  5/1997 Samad et al. ............ 210/764
7,282,475 B2* 10/2007 Porter et al. ............. 510/424

OTHER PUBLICATIONS

Deggerdal, Arne and Frank Larson. "Rapid Isolation of PCR-Ready DNA from Blood, Bone Marrow and Cultured Cells, Based on Paramagnetic Beads," BioTechniques (1997) 22: 554-557.
Rudi, K. et al. "Rapid, Universal Method to Isolate PCR-Ready DNA Using Magnetic Beads," BioTechniques (1997) 22: 506-511.
Taylor, Michael T. et al. "Lysing Bacterial Spores by Sonication through a Flexible Interface in a Microfluidic System," Analytical Chemistry (2001) 73: 492-496.

* cited by examiner

*Primary Examiner*—Jill Warden
*Assistant Examiner*—Dean Kwak
(74) *Attorney, Agent, or Firm*—Cantor Colburn LLP (57) ABSTRACT

Provided is a lysis method for cells or viruses, including: immobilizing a metal-ligand complex on a solid support; and mixing the complex immobilized on the support with a cell or virus solution. According to the lysis method, by immobilizing a chemical on a solid support to perform cell lysis, the dilution problem according to the addition of a cell lysis solution can be resolved and a separate process of removing the chemical is not required so as to reduce the steps upon LOC implementation. In addition, since a variety of solid supports, such as chips, beads, nanoparticles etc. can be used, cell lysis apparatuses of various forms can be fabricated.

11 Claims, 6 Drawing Sheets

CELL LYSIS METHOD BY IMMOBILIZED METAL-LIGAND COMPLEX

BACKGROUND OF THE INVENTION

This application claims the benefit of Korean Patent Application No. 2004-0090497, filed on Nov. 8, 2004, in the Korean Intellectual Property Office, the disclosure of which is incorporated herein in its entirety by reference.

1. Field of the Invention

The present invention relates to a cell lysis method by an immobilized metal-ligand complex.

2. Description of the Related Art

Isolation methods of DNA from cells were provided using materials that have the proclivity of binding to DNA. Examples materials of isolation methods of DNA are silica, glass fiber, anion exchange resin and magnetic beads (Rudi, K. et al., *Biotechniqures* 22, 506-511 (1997); and Deggerdal, A. et al., *Biotechniqures* 22, 554-557 (1997)). To avoid the manual steps and to remove operator error, several automatic machines were developed for high-throughput DNA extraction.

Cell lysis is conventionally performed by a mechanical, chemical, thermal, electrical, ultrasonic, and microwave method (Michael T. Taylor et al., *Anal.Chem.*, 73, 492-496 (2001)).

Heating is an alternative for disrupting cell walls or membranes. A disadvantage of simple heating is that it denatures proteins that can stick to the released DNA. They are likely to interfere with DNA amplification. A physical method is the use of a pressure apparatus, which is bulky and expensive, and thus, is not suitable for a Lab-On-a-Chip (LOC) application.

An ultrasonication is an alternative physical method; solutions or suspensions of cells are placed in a chamber placed in an ultrasonic bath. Ultrasonic disruption has many disadvantages in cell lysis. First of all, the energy distribution of ultrasonic is not uniform. The nonuniform distribution of ultrasonic energy leads to inconsistent results. Second, due to the energy divergence in the ultrasonic bath, it often takes several minutes to completely disrupt the cells. Lastly, ultrasonic method has unpleasant sound for human ears.

A chemical method includes the use of lysing agents for disrupting cells to release DNA. The lysing agents include detergents, alkaline treatments and chaotropic agents.

Detergents will disrupt the lipid bilayer allowing the contents to be released and will solubilize membrane proteins. It is most commonly used to lyse animal cells. Many detergents denature proteins. However, the addition of a cell lysis solution and the subsequent removal process are required and bubbles are generated. Thus, this method is not suitable for LOC implementation.

Alkaline treatments solubilize the phospholipid and protein components of the cell membrane. It is the easiest and least expensive chemical lysis method. Further, it is a fast, reliable and relatively clean way to obtain DNA from cells. However, the addition of an alkaline lysis solution for cell lysis and the neutralization process after lysis for DNA stabilization and the subsequent process application are required. Thus, steps upon LOC implementation are increased and the cell solution is diluted in direct proportion to the amount of the solution added.

Chaotropic agents having the ability to disrupt hydrophobic interactions may denature protein, but do not DNA or RNA. However, it is necessary to add a cell lysis solution to the chaotropic agent. Since the agent itself is very toxic and acts as a PCR inhibitor, the subsequent removal process is required. Thus, it is not suitable for LOC implementation.

Thus, the biggest problem in the conventional chemical lysis methods is that the addition of a lysis reagent allows a cell solution to be diluted, which results in an increase in the cell volume, and a separate removal process for removing the reagent should be performed after cell lysis is completed.

U.S. Pat. No. 5,304,487 discloses that physical protrusions in a microchannel or sharp-edged particles in a chamber or channel are used to mechanically lyse cells. Although there is a description of a solid support, there is no description of a method of lysing cells by immobilizing a metal-ligand complex on a solid support.

Thus, the inventors of the present invention discovered that a material having a cell lysis ability is immobilized on a solid surface to overcome the dilution problem resulting from the addition of the lysis solution and implement LOC without a separate process for removing the reagent in the course of studying a lysis method of cells or viruses on the basis of conventional technologies.

SUMMARY OF THE INVENTION

The present invention provides a cell lysis method by an immobilized metal-ligand complex, which can maintain the volume of a cell solution by dilution upon cell lysis and perform directly a polymerase chain reaction (PCR) without a removal process of a cell lysis substance after cell lysis to reduce steps upon LOC implementation.

According to an aspect of the present invention, there is provided a lysis method of cells or viruses, the method including: immobilizing a metal-ligand complex on a solid support; and mixing the complex immobilized on the solid support with a cell or virus solution.

In the method, the solid support may be selected from the group consisting of a slide glass, silicone wafer, magnetic bead, polystyrene, membrane, and metal plate.

In the method, a metal of the metal-ligand complex may be selected from the group consisting of transition metal ions, such as Cu (II), Co (III), Ni (II), Zn (II), and Fe (III).

In the method, a ligand of the metal-ligand complex may be selected from the group consisting of a cyclic polyamine compound, such as cyclene, an aliphatic polyamine compound, such as tris-(2-aminoethylamine), and a polycarboxy compound, such as EDTA.

In the method, the mixing may include vibrating a mixture of the complex and the cell or virus solution.

In the method, the vibrating may be performed by a vibrator selected from the group consisting of sonicators, vibrators using a magnetic field, vibrators using an electric field, and mechanical vibrators.

According to another aspect of the present invention, there is provided a lysis method of cells or viruses, the method including: immobilizing a metal-ligand complex on a solid support; immobilizing a chemical capable of interacting with cells or viruses on the solid support; and mixing the support having the complex and the chemical immobilized thereon with a cell or virus solution.

In the method, the chemical may be a compound having a functional group selected from the group consisting of a hydrophobic group, hydrophilic group, and a combination thereof.

In the method, the hydrophilic group may be selected from the group consisting of carboxylic acid, sulfonic acid, amine, and guanidine.

In the method, the hydrophobic group may be an aliphatic carbon chain or aromatic ring.

In the method, the solid support may be selected from the group consisting of a slide glass, silicone wafer, magnetic bead, polystyrene, membrane, and metal plate.

In the method, a metal of the metal-ligand complex may be selected from the group consisting of transition metal ions, such as Cu (II), Co (III), Ni (II), Zn (II), and Fe (III).

In the method, a ligand of the metal-ligand complex may be selected from the group consisting of a cyclic polyamine compound, such as cyclene, an aliphatic polyamine compound, such as tris-(2-aminoethylamine), and a polycarboxy compound, such as EDTA.

In the method, the mixing may include vibrating a mixture of the substrate and and the cell or virus solution.

In the method, the vibrating may be performed by a vibrator selected from the group consisting of sonicators, vibrators using a magnetic field, vibrators using an electric field, and mechanical vibrators.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in more detail.

The present invention relates to a lysis method of cells or viruses, the method including: immobilizing a metal-ligand complex on a solid support; and mixing the complex immobilized on the solid support with a cell or virus solution.

When the metal-ligand complex is immobilized on a solid support, such as a substrate or beads, water is coordinated to a metal ion of the immobilized metal-ligand complex. Then, the water is activated into a hydroxide ion. When the complex having the coordinated hydroxide ion is mixed with a cell or virus solution, the coordinated hydroxide ion lyses cells or viruses in the solution.

Figure 1:
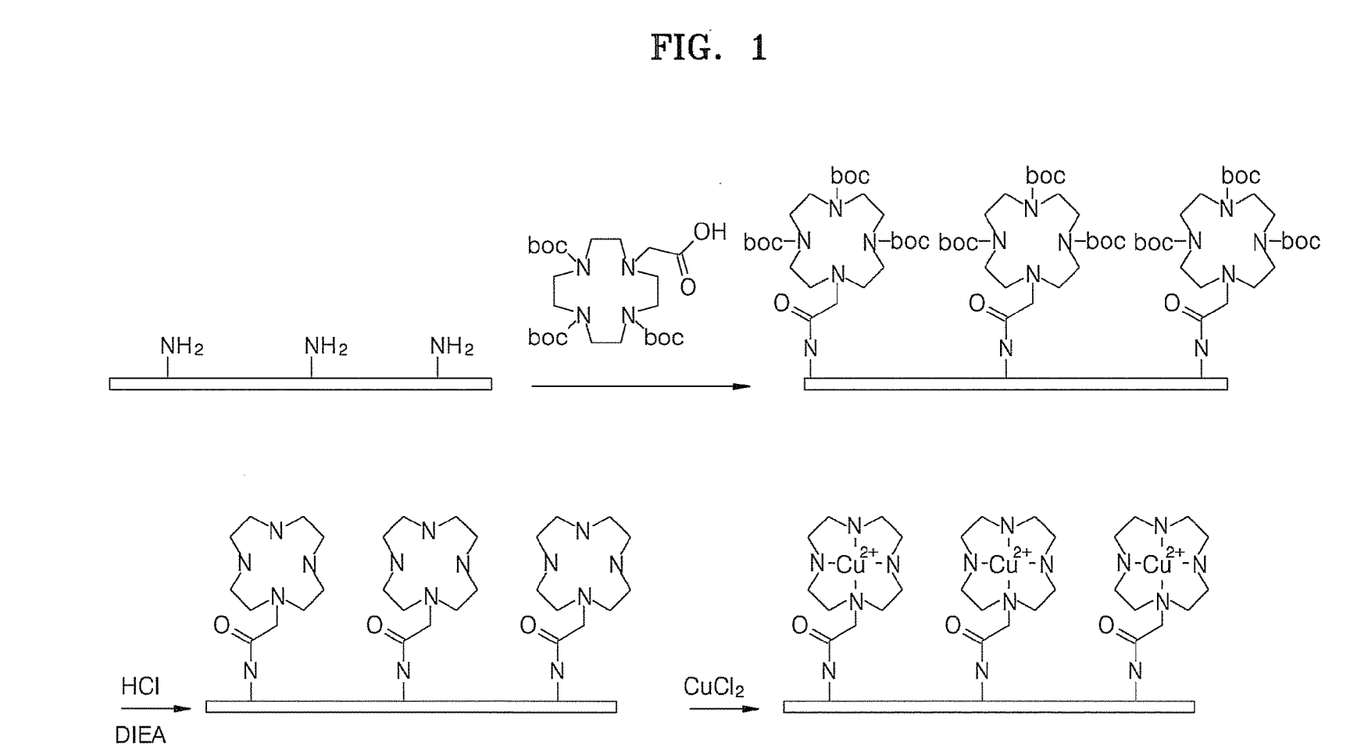
FIG. 1 illustrates an example of a process of immobilizing a Cu-cyclene (1,4,7,11-tetraazacyclododecane) complex on a glass substrate.

The technology of immobilizing a metal-ligand complex on a solid support is known in the art and can be exemplified by technology using a glass substrate as the solid support. FIG. 1 illustrates an example of a process of immobilizing a Cu-cyclene complex on a glass substrate. When the substrate is treated with cyclene as a ligand, the cyclene is bound to the substrate while dehydration occurs. Then, hydrochloric acid and diisopropylethylamine (DIEA) are added to the substrate to remove boc (t-butoxycarbonate) which acting as a protecting group, and then $CuCl_2$ is added thereto, thereby completing the Cu-cyclene complex.

Figure 2:
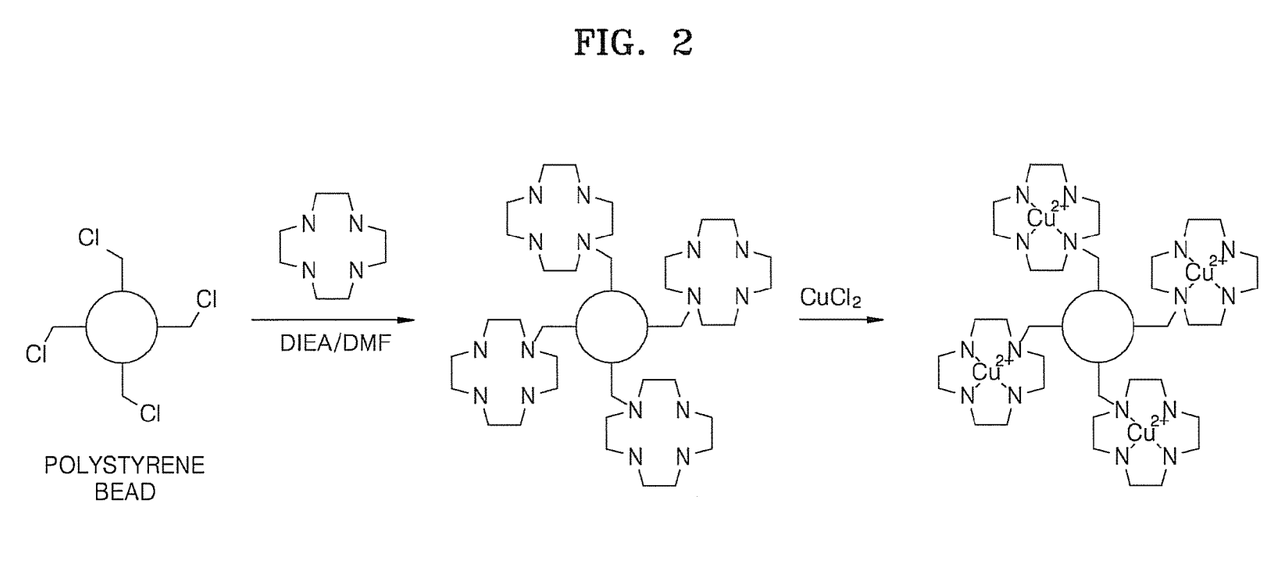
FIG. 2 illustrates an example of a process of immobilizing a Cu-cyclene complex on a polystyrene bead.

The known technology of immobilizing a metal-ligand complex on a solid support can be exemplified by technology using a bead as the solid support. FIG. 2 illustrates an example of a process of immobilizing a Cu-cyclene complex on a styrene bead. When a metal-ligand complex is immobilized on a flat substrate, the quantity of the metal-ligand complex introduced is small due to a small surface area of the substrate and the contact of the complex and cells or viruses is limited.

Thus, this method can increase the quantity of the metal-ligand complex introduced and the contact area of the solid support and cells by immobilizing the metal-ligand complex on a bead compared to when using a substrate. In the immobilization method, as illustrated in FIG. 2, when cyclene as a ligand and diisopropylethylamine (DIEA) dissolved in dimethylformamide (DMF) are added to a styrene bead, cyclene is bound to the bead. Then, $CuCl_2$ is added to the bead to complete the Cu-cyclene complex.

After the metal-ligand complex is immobilized on the solid support, a cell or virus solution is added. When the added cell or virus solution contacts the metal-ligand complex, a hydroxide ion coordinated to a metal ion acts as an active site to lyse a cell.

M= : Cu(II), Co(III)

In an embodiment of the present invention, the solid support can be selected from the group consisting of a slide glass, silicone wafer, magnetic bead, polystyrene, membrane, and metal plate. The solid support can be anything on which the metal-ligand complex can be immobilized. However, it should be insoluble in water. When it is soluble in water, it is difficult to separate a nucleic acid-containing solution from the solid support after cell lysis. The solid support having a large surface area is preferable because more metal-ligand complexes can be bound. To increase the surface area, a flat substrate, such as glass or wafer, can be surface-processed in a pillar form.

In an embodiment of the present invention, a metal of the metal-ligand complex can be selected from the group consisting of transition metal ions, such as Cu (II), Co (III), Ni (II), Zn (II), and Fe (III). Any metal capable of forming a complex with a ligand can be used.

In an embodiment of the present invention, a ligand of the metal-ligand complex can be selected from the group consisting of a cyclic polyamine compound, such as cyclene, an aliphatic polyamine compound, such as tris-(2-aminoethylamine), and a polycarboxy compound, such as EDTA. The ligand generally refers to an ion or molecule bound to a central atom in a complex compound, which is a compound having a lone pair. For example, in $[Co(NH_3)_6]Cl_3$, $K_3[FeCl_6]$, $[Cu(NH_2CH_2COO)_2]$ etc., $NH_3$, $Cl^-$, and $NH_2CH_2COO^-$ etc. are ligands as ions or molecules bound to central atoms $Co^{3+}$, $Fe^{3+}$, $Cu^{2+}$ etc., respectively. The ligand may be a single atomic ion or a polyatomic group.

In an embodiment of the present invention, the mixing can include vibrating a mixture of the complex and the cell or virus solution. When the cell or virus solution and the metal-ligand complex are left in a stagnant state, the probability of contact between the solution and the complex is decreased due to a reduction in the motion of the cells or viruses. Thus, the vibration is required to increase the probability of contact between the solution and the complex. The vibration can be performed by a vibrator selected from the group consisting of sonicators, vibrators using a magnetic field, vibrators using an electric field, and mechanical vibrators. Any apparatus capable of vibrating the solution and the complex can be used.

The present invention also relates to a lysis method of cells or viruses, the method including: immobilizing a metal-ligand complex on a solid support; immobilizing a chemical capable of interacting with the cells or viruses on the solid support; and mixing the support having the metal-ligand complex and the chemical immobilized thereon with a cell or virus solution.

In order to mix the metal-ligand complex and the cell or virus solution so as to lyse cells or viruses, the cells or viruses and the complex immobilized on the solid support should contact each other. The contact of cells or viruses and the complex can be promoted by immobilizing the chemical capable of interacting with the cells or viruses on the solid support. The chemical capable of interacting with the cells or viruses attracts the cells or viruses to a solid support on which the complex is immobilized, and thus increases the probability of contact between the cells or viruses and the complex. Owing to such an increase in the contact opportunity, lysis of cells or viruses increases. The interaction between the cells or viruses and the chemical can be performed by hydrophobic interaction, electrostatic interaction, hydrogen bonding, and the like.

In an embodiment of the present invention, the chemical can be a compound having a functional group selected from the group consisting of a hydrophobic group, hydrophilic group, and a combination thereof. A compound having a hydrophobic group can interact with the cells or viruses through hydrophobic interactions and a compound having hydrophilic group can interact with the cells or viruses through electrostatic interactions, hydrogen bonding, and the like. Examples of the compound having the hydrophobic group include aliphatic carbon compounds and aromatic carbon compounds. Examples of the compound having the hydrophilic group include amino acid derivatives. Examples of the chemical capable of interacting with viruses include a virus receptor, an antibody to a virus surface antigen, and the like.

In an embodiment of the present invention, the hydrophilic group can be selected from the group consisting of carboxylic acid, sulfonic acid, amine and guanidine. The functional group having a negative charge, such as carboxylate and sulfonate, can interact with a functional group having a positive charge on a cell or virus surface by electrostatic interaction or hydrogen-bond. The functional group having a positive charge, such as ammonium and guanidinium, can interact with a functional group having a negative charge on a cell or virus surface by electrostatic interaction or hydrogen-bond.

In an embodiment of the present invention, the hydrophobic group can be an aliphatic carbon chain or aromatic ring. A compound having the hydrophobic group can interact with a hydrophobic group on a cell or virus surface through hydrophobic interaction.

In an embodiment of the present invention, the solid support can be selected from the group consisting of a slide glass, silicone wafer, magnetic bead, polystyrene, membrane, and metal plate. The solid support can be anything on which the metal-ligand complex can be immobilized. However, it should be insoluble in water. When it is soluble in water, it is difficult to separate a nucleic acid containing solution from the solid support after cell lysis. A solid support having a large surface area is preferable because more metal-ligand complex can be bound. To increase the surface area, a flat substrate, such as glass or wafer, can be surface-processed in a pillar form.

In an embodiment of the present invention, a metal of the metal-ligand complex can be selected from the group consisting of transition metal ions such as Cu (II), Co (III), Ni (II), Zn (II), and Fe (III). Any metal capable of forming a complex with a ligand can be used.

In an embodiment of the present invention, a ligand of the metal-ligand complex can be selected from the group consisting of a cyclic polyamine compound, such as cyclene, an aliphatic polyamine compound such as tris-(2-aminoethylamine), and a polycarboxy compound such as EDTA. The ligand generally refers to an ion or molecule bound to a central atom in a complex compound, which is a compound having a lone pair. For example, in $[Co(NH_3)_6]Cl_3$, $K_3[FeCl_6]$, $[Cu(NH_2CH_2COO)_2]$ etc., $NH_3$, $Cl^-$, $NH_2CH_2COO^-$ etc. are ligands as ions or molecules bound to central atoms $Co^{3+}$, $Fe^{3+}$, $Cu^{2+}$ etc., respectively. The ligand may be a single atomic ion or polyatomic group.

In an embodiment of the present invention, the mixing can include vibrating a mixture of the support and the cell or virus solution. When the cell or virus solution and the metal-ligand complex are left in a mixed state, cells or viruses in the solution are settled at the bottom, and thus the probability of contact between the solution and the complex is decreased. Thus, vibration is required to increase the contact opportunity of the solution and the complex. The vibration can be performed by a vibrator selected from the group consisting of sonicators, vibrators using a magnetic field, vibrators using an electric field, and mechanical vibrators. Any apparatus capable of vibrating the solution and the complex can be used.

The present invention will now be described in greater detail with reference to the following examples. The following examples are for illustrative purposes only and are not intended to limit the scope of the invention.

EXAMPLES

Preparation Example 1

Immobilization of a Metal-Ligand Complex on a Substrate

To immobilize a metal-ligand complex on a substrate activated with an amino group, a glass substrate coated with ɣ-aminopropylsilane was used. 0.5 g of Cyclene protected by boc (t-butoxycarbonate) as a ligand and 0.2 g of HBTU were dissolved in 5 mL of DMF, and then the resulting solution was added to the glass substrate to immobilize the ligand on the substrate. Then, 5 mL of 0.1 M HCl was added to the substrate to remove the boc, the protecting group. The substrate was treated with 10% diisopropyleneamine solution to remove any salt. A solution of 0.1 g of $CuCl_2$ in DMF was added to the substrate to prepare a Cu-cyclene complex.

Preparation Example 2

Immobilization of a Metal-Ligand Complex on a Bead

To immobilize a metal-ligand complex on a bead, a polystyrene bead was used. 0.1 g of cyclene as a ligand and 10 mL of a solution of 10 μl of diisopropylethylamine in dimethylformamide were added to 1 g of a polystyrene bead activated with chloromethyl (Aldrich) to immobilize the ligand on the styrene bead. Then, a solution of 0.1 g of $CuCl_2$ in DMF was added to the bead to bind $Cu^{2+}$ to the cyclene, thereby preparing a Cu-cyclene complex immobilized on the bead.

Preparation Example 3

Bacteria, Primer and Polymerase Chain Reaction (PCR)

*E. coli* strains DH5α (3 mL), which were transformed with plasmids recombined with the HBV gene, were cultured at 37° C. with vigorous aeration in LB media (Sambrook et al., 1989) to exponential phase ($OD_{600}$=0.64). The bacterial cells were collected by centrifugation and twice washed with 3 mL of a phosphate buffered saline (PBS). The cells were resuspended in PBS (cell density: $1 \times 10^6$ cells/mL).

All PCRs were performed using the LightCycler instrument (Roche Diagnostics, Mannheim, Germany) in 20 µl. A forward primer (SEQ ID No: 1) and a reverse primer (SEQ ID No: 2) were used to amplify a core region of the HBV genome. A mastermix in the LightCycler reaction was prepared as follows: 2 µl LightCycler master (Fast start DNA master SYBR Green I; Roche Diagnostics), 3.2 µl $MgCl_2$ (5 mM), 1.0 µl forward-reverse primer mix (1.0 µM), 4.0 µl UNG (Uracil-N-Glycosylase, 0.2 unit), and 4.8 µl $H_2O$. 5 µl of the samples to be tested were added to the mastermix. Two types of Taq DNA polymerases (Roche Hot-start Taq DNA polymerase and Solgent Taq DNA polymerase) were used to prepare a LightCycler master.

In the case of the Roche Hot-start Taq DNA polymerase, after a pre-denaturation at 50° C. for 10 min and at 95° C. for 10 min, 35 cycles (denaturation at 95° C. for 5 sec, and annealing and extension at 62° C. for 15 sec) were performed. In the case of the Solgent Taq DNA polymerase, after a pre-denaturation at 50° C. for 10 min and 95° C. for 1 min, 35 cycles (denaturation at 95° C. for 5 sec, and annealing and extension at 62° C. for 15 sec) were performed.

The amplified DNA was analyzed in Agilent BioAnalyzer 2100 (Agilent Technologies, Palo Alto, Calif.) with a commercial available DNA 500 assay sizing reagent sets.

Preparation Example 4

Determination of Cell Viability

The number of living cells was determined by means of an ability of a single cell to form a colony. A recombinant *E. coli* stock solution (ATCC # 45020) or bacteria stock solution was spread on a LB (10 g/L tryptone, 5 g/L yeast extract, 15 g/L agar and 10 g/L NaCl) agar plate containing 50 mg/L of ampicillin. The plate was incubated at 37° C. for 12 hours. Then, the colony was removed from an agar plate surface and transferred to 10 mL LB medium having 50 mg/L ampicillin. 100 mL of cells were placed into a 100 mL shaking flask and incubated at 37° C., 250 rpm for 6-8 hours. Shake flask culture of *E. coli* cells was performed. The cells were washed with 1×PBS obtained from Gibco (NY, USA), resuspended, and then centrifuged using Eppendorf 5810R centrifuge (Eppendorf AG, Hamburg, Germany) at 6,000 g, 4° C. for 10 min.

A substrate or bead was used to lyse cells, and then the lysates were centrifuged at 13,200 rpm for 5 min. The supernatant was taken and the remaining precipitate was resuspended in 1×PBS. Then, the precipitate was spread on an agar plate and incubated at 37° C. for 12 hours. The formed colony was observed.

Example 1

Cell Lysis Effects of the Cu-Cyclene Complex Immobilized on a Substrate

To investigate the cell lysis effect of the Cu-cyclene complex immobilized on the substrate, the Cu-cyclene complex was treated with the cell solution prepared above ($1\times10^6$ cells/mL). First, bacterial cells were cultured and the cell solution and PBS were mixed at a ratio of 1:5. 60 µl of the mixture was applied to the substrate having the Cu-cyclene complex immobilized thereon at room temperature. Then, the substrate was vibrated at pH 7 and 9 at 50° C. for 20 min to lyse cells. After cell lysis, the lysate was separated and cells were precipitated by centrifuging. Then, the precipitated cells were resuspended and the cell viability was investigated.

Figure 3:
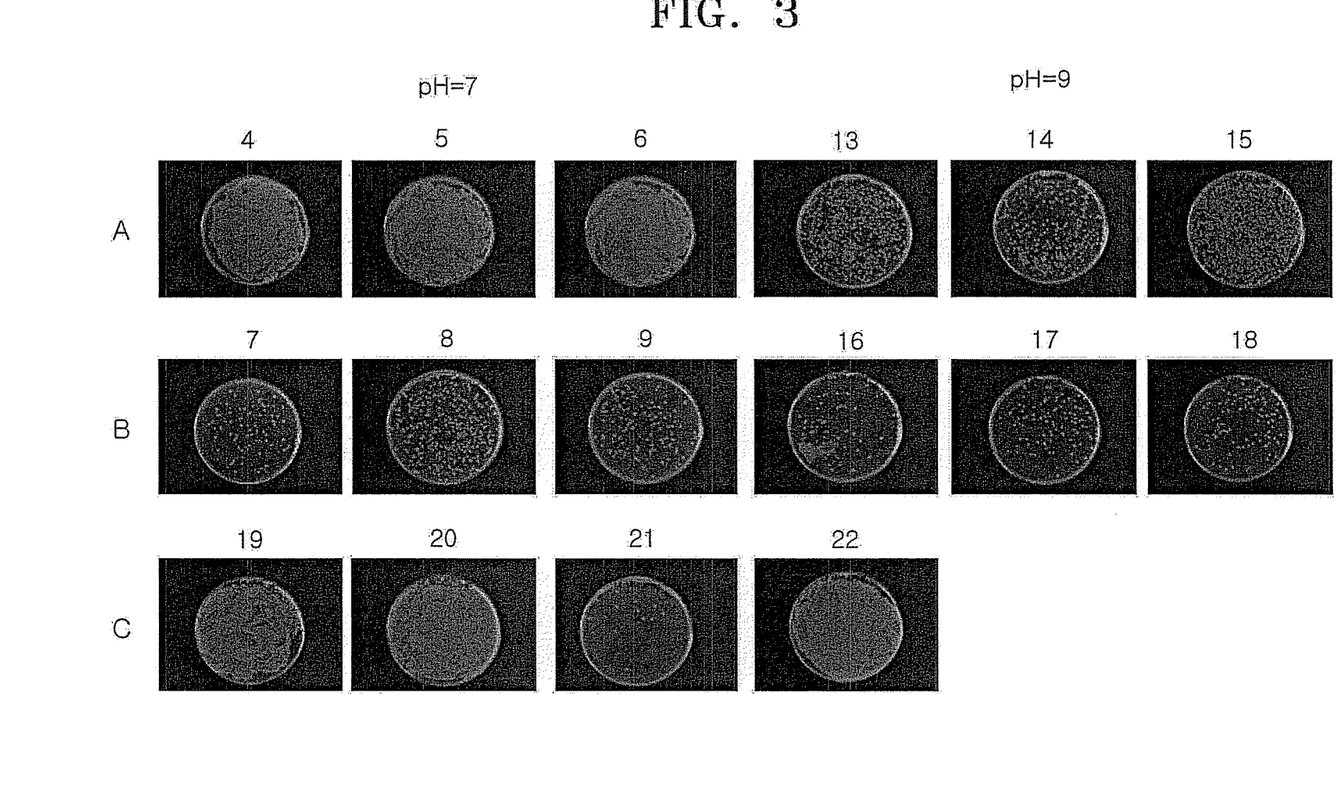
FIG. 3 shows the viability of cells after treating cells with a Cu-cyclene complex immobilized on a slide glass at pH 7 and 9.

FIG. 3 shows the cell viability after Cu-cyclene complex treatment at pH 7 and 9. Cells were lysed for the above lysis time at the presence of cyclene (panel A), in the presence of the Cu-cyclene complex (panel B), and at the presence of only the solution without a substrate (panel C), and then spread on LB plates. Experiments for the respective conditions were triply performed. The plates were incubated overnight at 37° C. and the number of the formed colonies wad scored.

Preparation methods of the respective samples were shown in the following Table.

| Plate No. | Substrate | pH |
|---|---|---|
| 4 | Cyclene | 7 |
| 5 | Cyclene | 7 |
| 6 | Cyclene | 7 |
| 7 | Cu-Cyclene | 7 |
| 8 | Cu-Cyclene | 7 |
| 9 | Cu-Cyclene | 7 |
| 13 | Cyclene | 9 |
| 14 | Cyclene | 9 |
| 15 | Cyclene | 9 |
| 16 | Cu-Cyclene | 9 |
| 17 | Cu-Cyclene | 9 |
| 18 | Cu-Cyclene | 9 |
| 19 | — | 7 |
| 20 | — | 9 |
| 21 | Boiling lysis | — |
| 22 | Positive control | — |

As shown in FIG. 3, when only cyclene was immobilized on the substrate (panel A), cells were hardly lysed (plate Nos. 4 to 6 (pH 7) and 13 to 15 (pH 9)). On the contrary, when the Cu-cyclene complex was immobilized (panel B), most cells were lysed, and thus the number of colonies was significantly reduced (plate Nos. 7 to 9 (pH 7) and 16 to 18 (pH 9)). When only the solution was added without a substrate (panel C), cells were hardly lysed (plate Nos. 19 and 20). When cells were lysed by boiling (at 95° C. for 1 min, at 40° C. for 30 sec, repeated 5 times) as a control group, most cells were lysed (plate No. 21). In the case of the positive control (plate No. 22) wherein the cell stock solution was directly spread on the plate without the above process, cells were hardly lysed. There seems no significant difference between the buffered solutions of pH 7 and 9.

Thus, it can be seen that in the case of the present invention where the Cu-cyclene complex was immobilized on the substrate the cell lysis efficiency was dramatically increased compared to when only cyclene was immobilized or only solution was present on the substrate. Of course, the cell lysis efficiency by boiling was also high, but it was difficult to apply it to LOC since it requires high temperatures.

Example 2

Cell Lysis Effects of the Cu-Cyclene Complex Immobilized on a Bead

To investigate the cell lysis effect of the Cu-cyclene complex immobilized on a bead, the Cu-cyclene complex was treated with the cell solution ($1\times10^6$ cells/mL). First, bacterial cells were cultured and two kinds of a stock solution and a 1/10 diluted solution were prepared as cell cultures. The two kinds of cell solutions and PBS were mixed at a ratio of 1:5, respectively. 60 µl of the mixture was applied to a styrene bead having the Cu-cyclene complex immobilized thereon at room temperature. Then, cells were lysed at 50° C. for 15 min at pH 7 and 9 while vibrating at intervals of 5 min. After cell lysis, the cells were precipitated by centrifuging. Then, the precipitated cells were resuspended and the cell viability was investigated.

Figure 4:
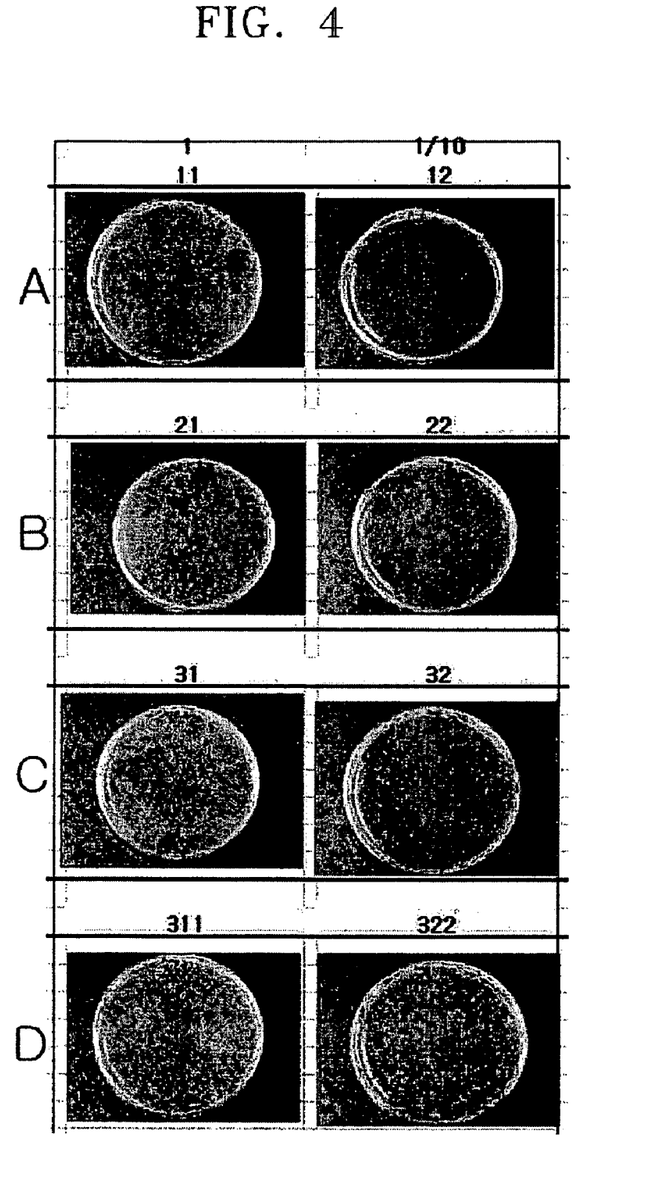
FIG. 4 shows the viability of cells after treating the cells with a Cu-cyclene complex immobilized on a polystyrene bead at pH 7.

FIG. 4 shows the cell viability after Cu-cyclene complex treatment at pH 7. Cells were lysed for the above lysis time at the presence of the Cu-cyclene complex (panel A), at the presence of only a bead without the Cu-cyclene complex (panel B), at the presence of only the solution (panel C) and a control group (panel D), and then spread on LB plates. The plates were incubated overnight at 37° C. and the number of the formed colonies was scored.

Preparation methods of the respective samples were shown in the following Table.

| Plate No. | Dilution level | Bead condition |
|---|---|---|
| 11 | Stock solution | Cu-cyclene-bead |
| 12 | 1/10 | Cu-cyclene-bead |
| 21 | Stock solution | Bead |
| 22 | 1/10 | Bead |
| 31 | Stock solution | Buffered saline |
| 32 | 1/10 | Buffered saline |
| 311 | Stock solution | Control |
| 322 | 1/10 | Control |

As shown in FIG. 4, when the Cu-cyclene complex was immobilized on the bead (panel A), most cells were lysed, and thus the number of colonies was significantly reduced (plate Nos. 11 and 12). On the contrary, when only the bead was used without immobilization of a Cu-cyclene complex (panel B), cells were rarely lysed (plate Nos. 21 and 22). When only the solution was added without a bead (panel C), cells were hardly lysed (plate Nos. 31 and 32). In the case of the control group wherein the cell storage solution was directly spread on the plate without the above process, cells were hardly lysed.

Thus, it can be seen that in the case of the present invention where the Cu-cyclene complex was immobilized on the bead, the cell lysis efficiency was dramatically increased compared to when only the bead was used or only the solution without a bead was present.

Example 3

DNA Release Effects of the Cu-Cyclene Complex Immobilized on the Bead

Figure 5:
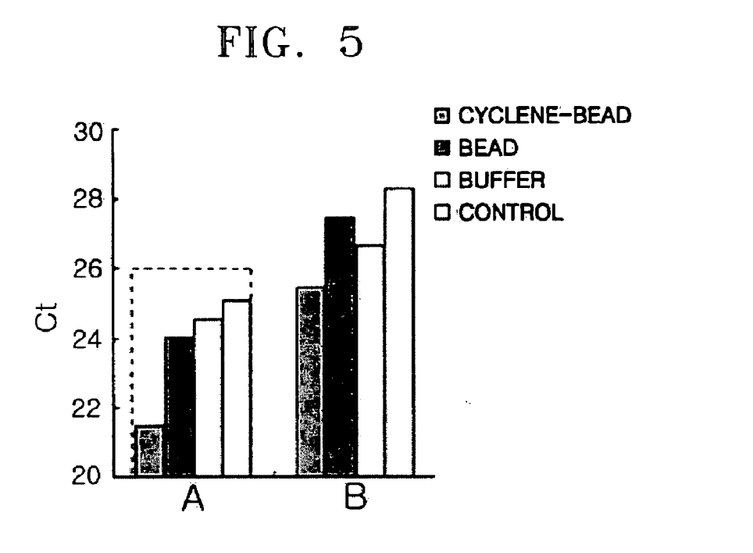
FIG. 5 illustrates the PCR results according to sample preparation methods as Count of threshold (Ct)

To confirm whether the Cu-cyclene complex immobilized on the bead efficiently releases DNA from cells, the quantity of DNA present in the cell lysate was investigated using a PCR. Cells were lysed by the methods described in Examples 1 and 2, and then a real-time PCR was performed using the supernatant. FIG. 5 illustrates the PCR results according to the sample preparation methods as Count of threshold (Ct). A is the results of using the cell culture stock solution and B is the results of using a 1/10 diluted solution of the cell culture. Ct representing the PCR results refers to the number of cycle at which an initial fluorescent signal appears in the real-time PCR. As the initial template DNA molecules are more at the PCR, the Ct is lower. As the DNA molecules are less, the Ct is higher. As shown in FIG. 5, in the case of the present invention using the Cu-cyclene-bead, the Ct value is very low compared to when a bead without Cu-cyclene immobilized was used, only a buffered saline without a bead was used or the cell stock solution was directly used as a control group. In the case of the 1/10 diluted solution (B), there was no significant difference in Ct values, but the present invention has a relatively low Ct value compared to the other sample preparation methods.

Figure 6:
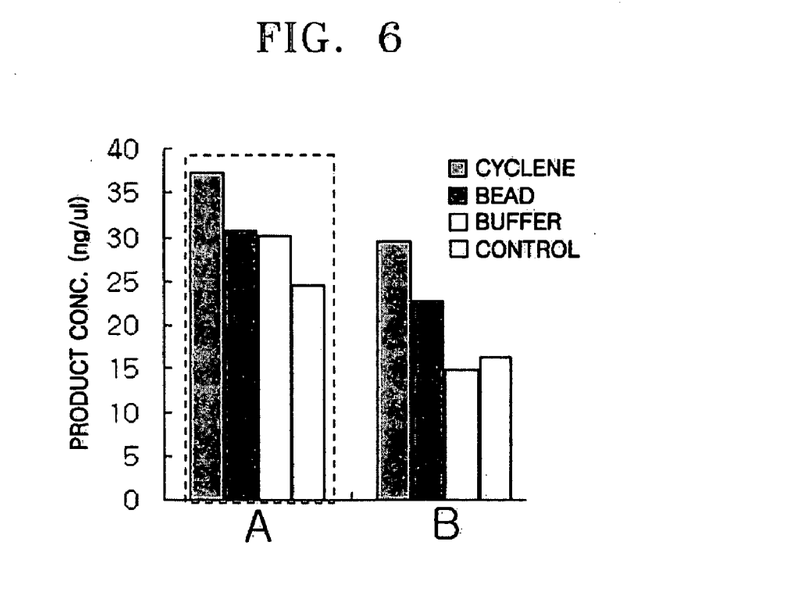
FIG. 6 illustrates the concentration of DNA amplified by a PCR according to sample preparation methods.

To investigate whether the Ct values had a direct correlation with the production of the desired PCR product, i.e., to confirm whether Ct values were lowered due to a lot of the desired PCR product, the concentration of the desired PCR product was measured. FIG. 6 illustrates the concentration of DNA amplified by PCR according to sample preparation methods. A is the results of using the cell culture stock solution and B is the results of using the 1/10 diluted solution of the cell culture. The bars represent the concentration (ng/μl) of the amplified DNA. The amount of the PCR product was quantified using Agilent BioAnalyzer 2100. As shown in FIG. 6, it can be seen that in the case of the present invention using the Cu-cyclene-bead, both the cell culture stock solution (A) and 1/10 diluted solution (B) had relatively more PCR products compared to when a bead without Cu-cyclene immobilized was used, only a buffered saline without a bead was used or the cell stock solution was directly used as a control group.

Thus, the above results mean that the present invention using the Cu-cyclene-bead had a higher concentration of the initial DNA by cell lysis than the other methods, indicating that cells were efficiently lysed.

Example 4

Figure 7:
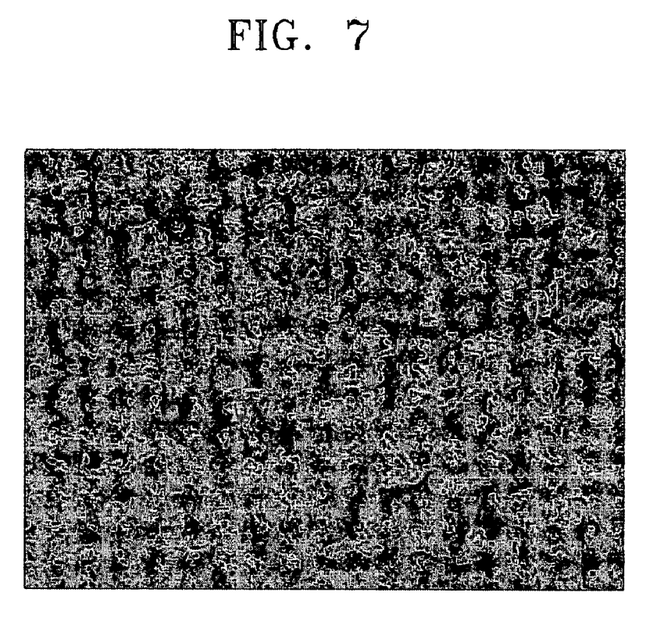
FIG. 7 is a photograph of cells bound to a substrate surface after applying an *E. coli* solution to a glass substrate, on which a carboxylic group capable of interacting with cells is introduced, and dyeing the substrate.

Interaction Between a Glass Substrate Having a Carboxylic Group Introduced and Cells To investigate the interaction between a glass substrate having a carboxylic group introduced and cells, E. coli cells were used. FIG. 7 is a photograph of cells bound to a substrate surface after applying 60 μl of an E. coli solution to the glass substrate, in which a carboxylic group capable of interacting with cells was introduced, and dyeing with a dye for dyeing E. coli known in the art. As shown in FIG. 7, it can be confirmed that cells are attached to the glass substrate surface having a carboxylic group introduced. Thus, when a carboxylic group and a Cu-cyclene complex are simultaneously introduced to a glass substrate or bead, cells are more easily attracted to the surface by the interaction between the cells and the carboxylic group. Therefore, since a probability of a reaction of Cu-cyclene and cells increases, it is expected that a higher cell lysis efficiency would be shown.

According to the present invention, by immobilizing a chemical on a solid support to perform cell lysis, the dilution problem according to the addition of cell lysis solution can be resolved and a separate process of removing the chemical is not required so as to reduce the steps upon LOC implementation. Moreover, cell lysis can be performed at a relatively mild condition (pH 7.0, 50° C.) and application in other chemical reactions, such as protein decomposition, besides the cell lysis through the modification of the chemical is possible. In addition, since a variety of solid supports, such as a chip, bead, nanoparticle etc. can be used, cell lysis apparatuses of various forms can be fabricated.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A lysis method of cells or viruses, comprising:
   immobilizing a metal-ligand complex on a solid support, wherein the metal of the metal-ligand complex is a transition metal ion selected from the group consisting of Cu (II), Co (III), Ni (II), Zn (II), and Fe (III), and
   wherein the ligand of the metal-ligand complex is selected from the group consisting of a cyclic polyamine compound and an aliphatic polyamine compound, wherein the cyclic polyamine is cyclene and the aliphatic polyamine compound is tris-(2-aminoethylamine); and
   mixing the complex immobilized on the support with a cell or virus solution.

2. The method of claim 1, wherein the solid support is selected from the group consisting of a slide glass, silicone wafer, magnetic bead, polystyrene, membrane, and metal plate.

3. The method of claim 1, wherein the mixing comprises vibrating the mixture of the complex and the solution.

4. The method of claim 3, wherein the vibrating is performed by a vibrator selected from the group consisting of sonicators, vibrators using a magnetic field, vibrators using an electric field, and mechanical vibrators.

5. A lysis method of cells or viruses, comprising:
immobilizing a metal-ligand complex on a solid support, wherein the metal of the metal-ligand complex is a transition metal ion selected from the group consisting of Cu (II), Co (III), Ni (II), Zn (II), and Fe (III), and
wherein the ligand of the metal-ligand complex is selected from the group consisting of a cyclic polyamine compound and an aliphatic polyamine compound, wherein the cyclic polyamine compound is cyclene and the aliphatic polyamine compound is tris-(2-aminoethylamine);
immobilizing a chemical capable of interacting with cells or viruses on the solid support; and
mixing the support having the complex and the chemical immobilized thereon with a cell or virus solution.

6. The method of claim 5, wherein the chemical includes a functional group selected from the group consisting of a hydrophobic group, hydrophilic group, and a combination thereof.

7. The method of claim 6, wherein the hydrophilic group is selected from the group consisting of carboxylic acid, sulfonic acid, amine, and guanidine.

8. The method of claim 6, wherein the hydrophobic group is an aliphatic carbon chain or aromatic ring.

9. The method of claim 5, wherein the solid support is selected from the group consisting of a slide glass, silicone wafer, magnetic bead, polystyrene, membrane, and metal plate.

10. The method of claim 5, wherein the mixing comprises vibrating the mixture of the support and the solution.

11. The method of claim 10, wherein the vibrating is performed by a vibrator selected from the group consisting of sonicators, vibrators using a magnetic field, vibrators using an electric field, and mechanical vibrators.

* * * * *